United States Patent
Rattner

(10) Patent No.: US 10,624,573 B2
(45) Date of Patent: Apr. 21, 2020

(54) SUNSCREEN VERIFICATION DEVICE

(71) Applicant: Sergio Rattner, Toronto (CA)

(72) Inventor: Sergio Rattner, Toronto (CA)

(73) Assignee: FITSKIN INC., Toronto (CA)

(*) Notice: Subject to any disclaimer, the term of this patent is extended or adjusted under 35 U.S.C. 154(b) by 0 days.

(21) Appl. No.: 16/051,420

(22) Filed: Jul. 31, 2018

(65) Prior Publication Data
US 2019/0038211 A1 Feb. 7, 2019

Related U.S. Application Data

(60) Provisional application No. 62/539,862, filed on Aug. 1, 2017, provisional application No. 62/598,064, filed on Dec. 13, 2017.

(51) Int. Cl.
| | |
|---|---|
| *A61B 5/00* | (2006.01) |
| *G01J 1/42* | (2006.01) |
| *G06F 1/16* | (2006.01) |
| *G01J 1/02* | (2006.01) |
| *G01J 3/50* | (2006.01) |
| *G01J 3/02* | (2006.01) |

(Continued)

(52) U.S. Cl.
CPC .......... *A61B 5/443* (2013.01); *A61B 5/6802* (2013.01); *G01J 1/0233* (2013.01); *G01J 1/429* (2013.01); *G01J 3/0262* (2013.01); *G01J 3/0272* (2013.01); *G01J 3/10* (2013.01); *G01J 3/42* (2013.01); *G01J 3/501* (2013.01); *G06F 1/1626* (2013.01); *G06F 1/1656* (2013.01); *G06F 1/1684* (2013.01); *G06F 1/1698* (2013.01); *G06F 2200/1633* (2013.01)

(58) Field of Classification Search
CPC .......... A61B 5/443; A61B 5/6802; G01J 3/10; G01J 3/0272; G01J 3/0262; G01J 3/501; G01J 3/42; G01J 1/429; G01J 1/0233; G06F 1/1698
USPC ....................................................... 250/372
See application file for complete search history.

(56) References Cited

U.S. PATENT DOCUMENTS

2008/0265170 A1* 10/2008 Ales ..................... A61B 5/0059
250/372

OTHER PUBLICATIONS

Hupel et al. "Development of a new in vitro method to evaluate the photoprotective sunscreen activity of plant extracts against high UV-B radiation", Talanta 86 (2011) 362-371. Year 2011.*

* cited by examiner

*Primary Examiner* — David P Porta
*Assistant Examiner* — Meenakshi S Sahu
(74) *Attorney, Agent, or Firm* — Elan IP Inc.

(57) ABSTRACT

There is a sunscreen detection device for detecting a sunscreen product, the sunscreen detection device comprising: a substrate; a first light, disposed on the substrate and controllably coupled to a processor, controllable by the processor to emit light at a first light wavelength at the subject's skin when the sunscreen detection device is oriented to emit light on the subject's skin; a first light sensor circuit, disposed on the substrate and communicatively coupled to the processor, capable of sensing a percentage absorption of light by the subject's skin at the first light wavelength (% AbsAtWL1) and communicating the % AbsAtWL1 to the processor; a processor, configured to: cause the first light to emit light when the sunscreen detection device is oriented to emit light on the subject's skin;

(Continued)

record the % AbsAtWL1 from the first light sensor; and assess a level of sunscreen protection based at least on the % AbsAtWL1.

17 Claims, 4 Drawing Sheets

(51) Int. Cl.
    *G01J 3/10*         (2006.01)
    *G01J 3/42*         (2006.01)

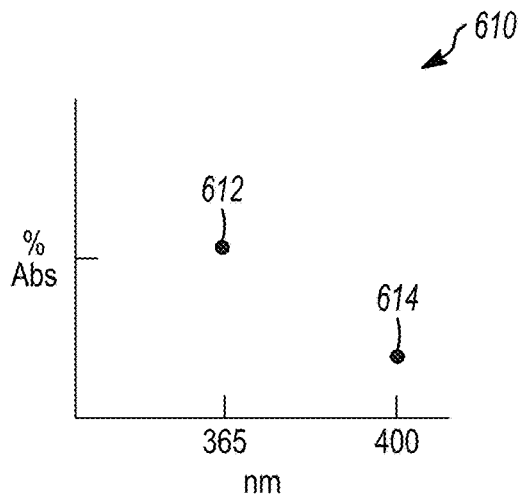
FIG. 6A
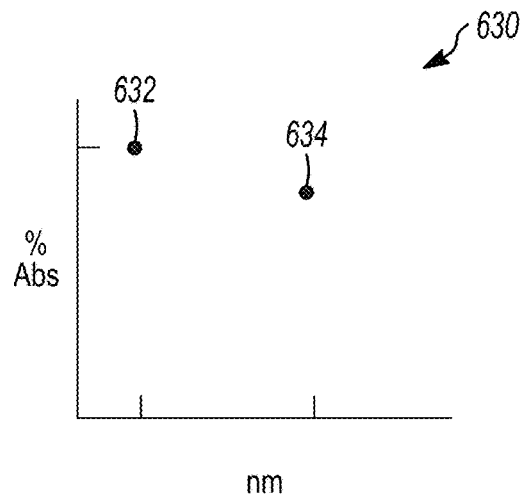
FIG. 6B
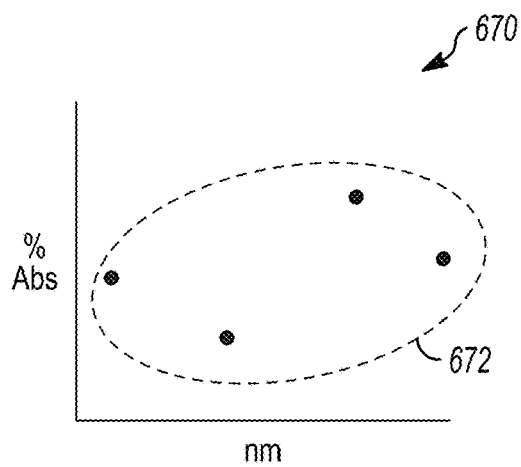
FIG. 6C
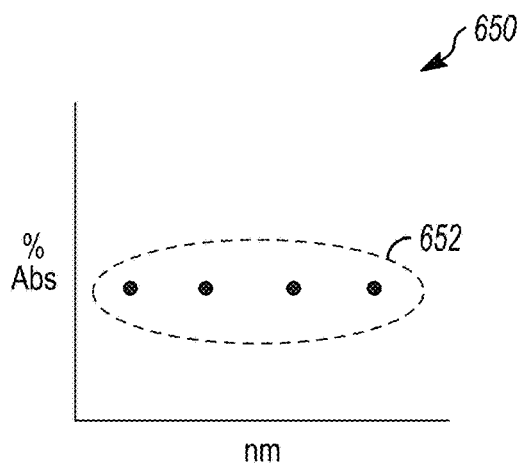
FIG. 6D
Get sunscreen signature — 702
Expose skin to light(s) based on sunscreen signature — 704
Measure absorption of light(s) — 706
Compare measured absorption — 708
FIG. 7

SUNSCREEN VERIFICATION DEVICE

CROSS-REFERENCE TO RELATED APPLICATIONS

This application claims priority from U.S. Provisional Application No. 62/539,862, filed on Aug. 1, 2017, and from U.S. Provisional Application No. 62/598,064, filed on Dec. 13, 2017, the contents of both of which, in their entirety, are herein incorporated by reference.

BACKGROUND

Sunscreen is a common term for skin care products that absorb UV radiation and dissipate it as heat.

Ultraviolet radiation arrives at the skin most often in three distinct wavelengths, designated UV-A, -B, and -C. UV-A has the longest wavelength at 400 nm-320 nm and therefore penetrates deeper into skin than the others, causing age spots and wrinkling, UV-B, with a wavelength of 320 nm-290 nm, is the primary cause of sunburns and the targeted range for protection, though Broad-spectrum sunscreens will inhibit both UV-A and UV-B. UV-C has a wavelength of 290 nm-100 nm, though it is completely blocked by the ozone layer.

Sunscreen is applied. After a period of time, the sunscreen wears off and its effectiveness diminishes, until the skin has lost all protection. The amount of time for this to occur depends on several factors: exposure to sun, amount of sunscreen applied initially, moisture in the air or skin, and the wearer's amount of physical activity.

The ability to detect if sufficient sunscreen has been applied to a particular skin area, and the ability to detect if the sunscreen is providing adequate protection, are two of the biggest challenges when using sunscreen. Neither sunscreen nor UV light are visible to the eye, making it difficult for consumers to tell if they have applied sufficient sunscreen, and whether it is providing adequate protection over the duration of sun exposure.

There thus remains a need for a low cost, easy to use device that tells a user whether they have applied enough sunscreen to their skin.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF THE INVENTION

The invention relates to devices for detecting sunscreen coverage.

SUMMARY OF THE INVENTION

There is a sunscreen detection device for detecting the presence of a sunscreen product on a subject's skin, the sunscreen detection device comprising: a substrate; a first light, disposed on the substrate and controllably coupled to a processor, controllable by the processor to emit light at a first light wavelength at the subject's skin when the sunscreen detection device is oriented to emit light on the subject's skin; a first light sensor circuit, disposed on the substrate and communicatively coupled to the processor, capable of sensing a percentage absorption of light by the subject's skin at the first light wavelength (% AbsAtWL1) and communicating the % AbsAtWL1 to the processor; a processor, configured to: cause the first light to emit light when the sunscreen detection device is oriented to emit light on the subject's skin; record the % AbsAtWL1 from the first light sensor; assess a level of sunscreen protection based at least on the % AbsAtWL1; and communicate the level of sunscreen protection.

The level of sunscreen protection may be "sufficient" if % AbsAtWL1 exceeds a first sunscreen reapplication threshold.

The processor may be further configured to: receive a skin color for the subject, the skin color indicating a threshold percentage absorption of light by the subject's skin at the first light wavelength (% ThAtWL1); and wherein the assessing is further based on the % ThAtWL1.

The level of sunscreen protection may be "sufficient" if % AbsAtWL1 exceeds % ThAtWL1 by a second sunscreen reapplication threshold.

The receiving may be from an input method on the sunscreen device.

The receiving may be from an app on a user's smartphone, the app being configured to send the skin color to the processor on the sunscreen protection device.

The sunscreen detection device may further comprise a second light, disposed on the substrate and controllably coupled to a processor, controllable by the processor to emit light at a second light wavelength at the subject's skin when the sunscreen detection device is oriented to emit light on the subject's skin; a second light sensor, disposed on the substrate and communicatively coupled to the processor, capable of sensing a percentage absorption of light by the subject's skin at the second light wavelength (% AbsAtWL2) and communicating the % AbsAtWL2 to the processor; wherein the processor may be further configured to: initiate the second light to emit light when the sunscreen detection device is oriented to emit light on the subject's skin; obtain the % AbsAtWL2 from the second light sensor; and wherein the assessing is further based on the % AbsAtWL2.

The assessing may further comprise calculating a skin absorption ratio equal to % AbsAtWL1 divided by % AbsAtWL2 and if the skin absorption ratio is about 1 then the level of sunscreen protection is insufficient and if the skin absorption ratio is greater than 2 or less than 0.5 then the level of sunscreen protection is sufficient.

The sunscreen detection device may further comprise an indicator light capable of producing a set of colors, mounted on the substrate and controllable by the processor and wherein the communicating further comprises the processor lighting the indicator light based on the level of sunscreen protection.

The substrate may be a round disc, the round disc shaped for installation within a cap of a sunscreen product bottle.

The sunscreen detection device may further comprise a cover, wherein the substrate is integrated into the cover, the cover being removably attached to a smartphone.

The cover may further comprise a slide, and wherein the substrate may slideably integrated into the cover and is attached to a slide, and the slide is slideable from an active position, where the sunscreen device is in use, and an inactive position, where the sunscreen device is not in use.

There is also a method for detecting the presence of a sunscreen product on a subject's skin, the sunscreen detection device comprising: exposing a subject's skin to a first light at a first wavelength and a second light at a second wavelength, the first light and the second light being mounted on, and controllable by, the sunscreen detection device; measuring, by a first light sensor and a second light sensor on the sunscreen detection device, an absorption of the first light and an absorption of the second light; and comparing, by a processor on the sunscreen detection device, the absorption of the first light and the absorption of the second light to determine a level of sunscreen protection.

The comparing may comprise calculating a skin absorption ratio equal to the absorption of the first light divided by the absorption of the second light and if the skin absorption ratio is about 1 then the level of sunscreen protection is insufficient.

The method may further comprise: receiving, by a sunscreen detection device, a sunscreen signature for the sunscreen product, the sunscreen signature comprising the sunscreen product's absorption of light at the first wavelength and the sunscreen product's absorption of light at the second wavelength; and wherein the comparing may further comprise using the sunscreen signature to determine a level of sunscreen protection.

The using may further comprise: calculating a sunscreen signature ratio as the sunscreen product's absorption of light at the first wavelength divided by the sunscreen product's absorption of light at the second wavelength; and contrasting the sunscreen signature ratio with the skin absorption ratio and if a difference between the ratios is a material amount then the level of sunscreen protection is insufficient.

The contrasting may further comprise ensuring that the skin absorption ratio is greater than a sunscreen reapplication threshold.

The receiving may further comprise: accepting, on an app on a user's smartphone, a user selection of an applied sunscreen product that the user believes they applied; locating, by the app on a user's smartphone, the sunscreen signature for the applied sunscreen product; and sending, by the user's smartphone to the sunscreen detection device, the sunscreen signature for the applied sunscreen product to be set as the sunscreen signature for the sunscreen product.

The method may further comprise: selecting, by a processor on the sunscreen detection device, the first wavelength and the second wavelength based on the sunscreen signature.

The selecting may further comprise ensuring the sunscreen product's absorption of light at the first wavelength and the sunscreen product's absorption of light at the second wavelength are different.

BRIEF DESCRIPTION OF THE DRAWINGS

The invention is illustrated in the figures of the accompanying drawings which are meant to be exemplary and not limiting, in which like references are intended to refer to like or corresponding parts, and in which:

FIGS. 6A-D show four graphs of sunscreen signatures, for sunscreen products A-D, according to an aspect of the invention;

FIG. 7 shows a method of determining sunscreen coverage, according to an aspect of the invention.

DETAILED DESCRIPTION OF THE PREFERRED EMBODIMENTS

Figure 1:
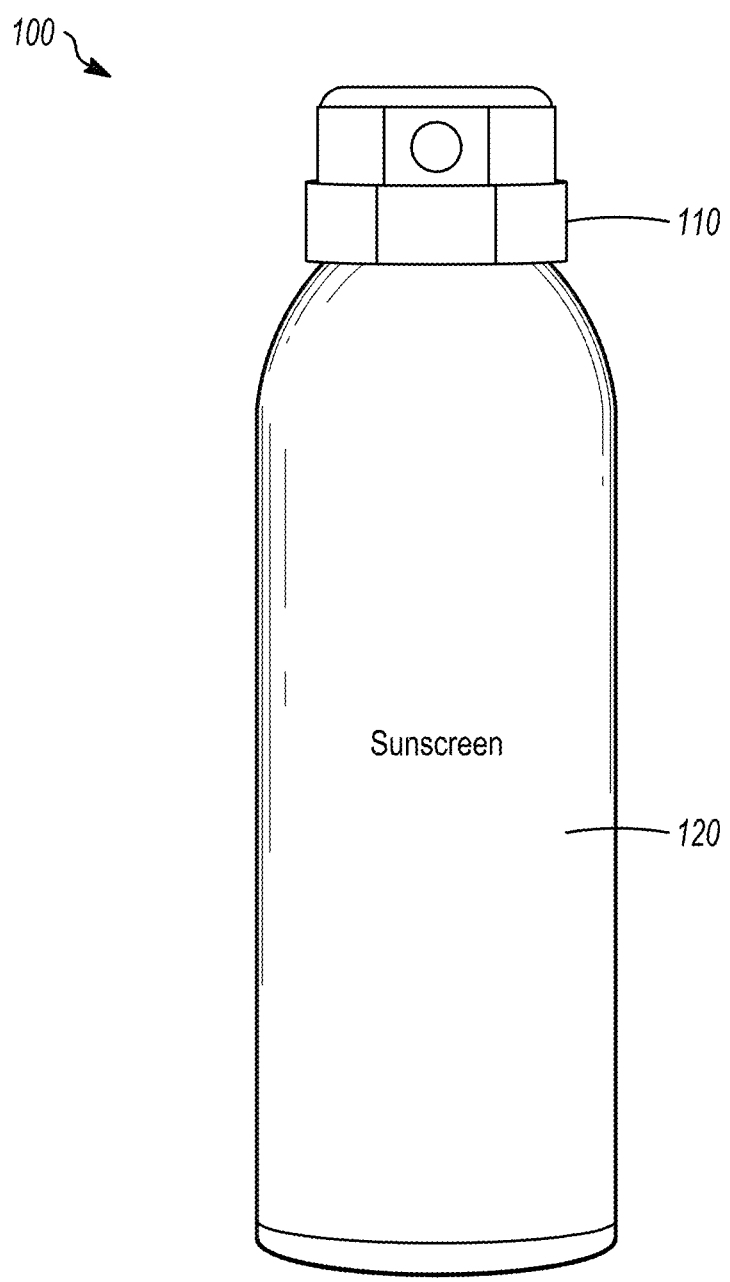
FIG. 1 is a depiction of a typical sunscreen product bottle.

FIG. 1 is a depiction of a typical sunscreen product bottle 100 have a sunscreen product section 120 holding a sunscreen product. The Device 200 could be installed within the cap 110, as part of the bottle 100, or as a standalone unit that could be used as a keychain, among other possibilities.

The Device (sunscreen measuring device or sunscreen detection device) 200 (and in particular substrate 230) can be made in the shape and size (e.g., round, disc, for example 0.5" dia.) of a threaded sunscreen product bottle cap. In this way, the device is always present when the user wants to apply and check sunscreen. When the cap 110 is unscrewed, the sunscreen product can be released. Within the cap 110 is the Device 200 which performs the functions described herein.

The Device may take skin color into account automatically (when coupled with the automatic skin color detection feature as first described in U.S. Provisional Application No. 62/438,835, filed on Dec. 23, 2016, U.S. Provisional Application No. 62/344,287 filed on Jun. 1, 2016, and U.S. Provisional Application No. 62/326,558 filed on Apr. 22, 2016; and in SYSTEMS AND METHOD FOR SKIN ANALYSIS USING ELECTRONIC DEVICES; No.: PCT/CA2017/050503 filed on Apr. 27, 2017).

Alternatively, the user's skin color can also be manually entered by the user via a smartphone app (not shown) on a smartphone 420 that can communicate with the Device 200, or another input method (e.g., rotary or sliding switch, keypad) on the Device 200 itself.

Skin color information is required in order to adjust the measurement sensitivity. The darker the skin, the more UV radiation is absorbed naturally.

The Device 200 works in the following way:
1) It is activated by pressing the on/off switch, or by using a skin detection system (such as a moisture or proximity sensor, not shown).
2) One or more UV lights turn on and shine on the skin. The UV LEDs have a known wavelength in the UV A and/or UV B spectrum. Note that light outside UV may also be employed, such as blue light.
3) One or more UV sensor(s) measures the amount of reflected light that bounces off the skin.
4) A warning light or message in a software application, such as in an app on smartphone 420, tells the user if the level of sunscreen at that point on the skin is sufficient.
5) Usage data may be collected and shared with the sunscreen manufacturer. Examples of collected data include but are not limited to: consumer sex, age, GPS location, weather at location, sunscreen application time, number of checks, number of times protection was exceeded, sunscreen products used, consumer feedback.

Figure 4:
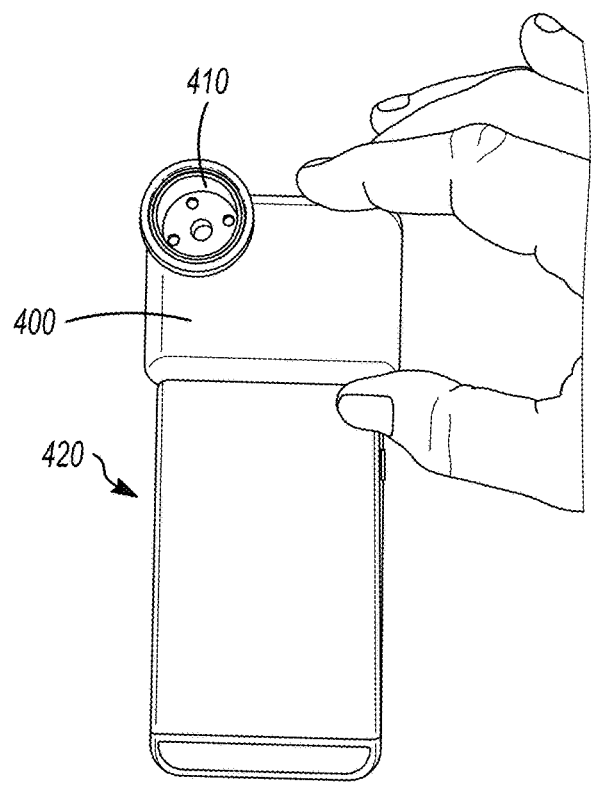
FIG. 4 shows the sunscreen measuring device attached to and operating in conjunction with a mobile device, according to an aspect of the invention.

6) Sunscreen product recommendations tailored on the consumer's skin type or level of exposure (e.g., if the protection level is exceeded, a higher SPF sunscreen can be recommended).
7) When coupled to the mobile device, as in FIG. 4, the operation is the same as described above, with the added benefit of automatic skin color detection.

The Device may be pre-programmed with varying threshold levels of sunscreen absorption for different skin tones (which may be used to set various sunscreen reapplication thresholds), and levels of absorption for the same skin tones with no sunscreen.

EXAMPLE

White skin/Reflection Threshold (no sunscreen)
=27%/Reflection Threshold (with sunscreen)
=14%

Black skin/Reflection Threshold (no sunscreen)
=17%/Reflection Threshold (with sunscreen)
=10%

The Device compares the actual reflection % to these Reflection Thresholds, to determine whether or not there is sufficient sunscreen applied in the measurement area.
In practice, Thresholds would exist for more than two skin colors.
Reflection is measured by UV detection circuit, an example of which is the Vishay VEML6075. These work by converting UV light intensity into digital data. A sensor with a peak sensitivity of a similar wavelength of light to the source UV lights is selected. The sensor's output voltage determines the intensity of UV light that it detects. The Device is initially calibrated with a mirror or foil (representing ~100% light reflection, and in a dark room (representing ~0% light reflection). The Thresholds above are then determined against several human skin examples. A manufacturer of sunscreen could adjust the Thresholds to levels they are comfortable with (e.g., a more cautious setting would alert the user to reapply or go indoors at a higher Reflection %).

Figure 2:
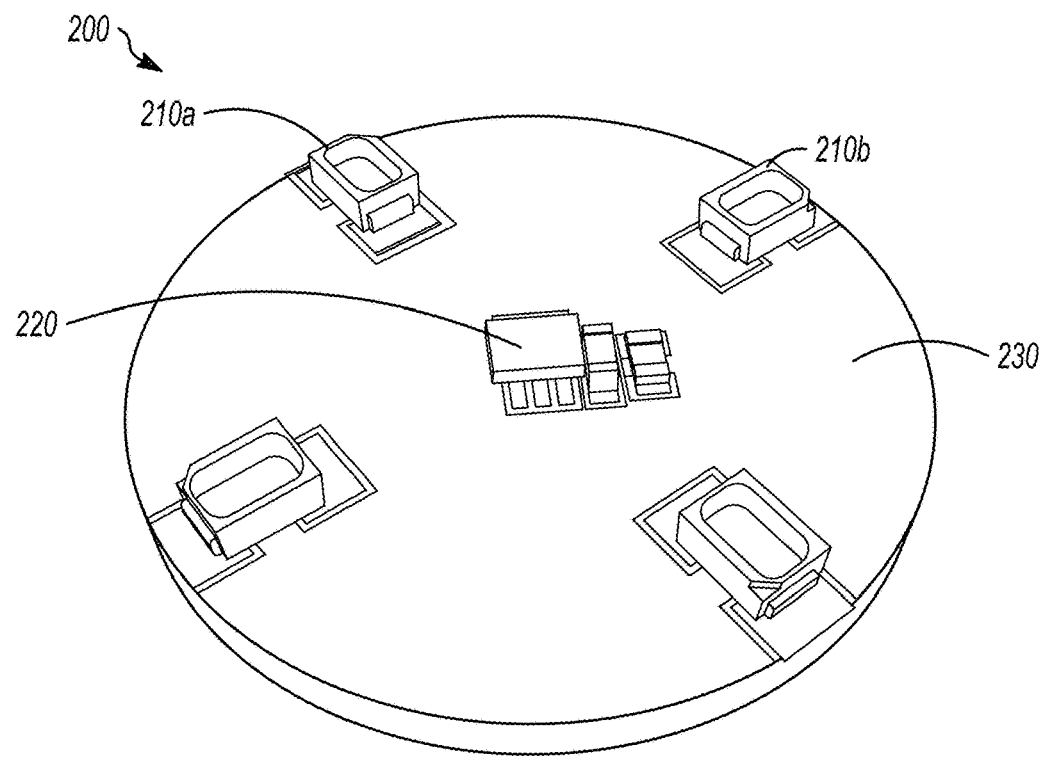
FIG. 2 shows the skin facing side of the device, according to an aspect of the invention.

FIG. 2 shows the skin facing side of the Device. Item 210a and 210b represents the UV LED(s) lights which can be one or several (four are shown) and emit light at one or more wavelengths. Such wavelengths may be chosen based on sunscreen signatures and may be determined by the sunscreen device's processor and/or by a subject's smartphone app. Item 220 represents the UV detection sensor (e.g., Vishay VEML6075), which can be one or several (one is shown, more may be desired if more than one wavelength of light is being used). Ultraviolet light sensor circuit 220 and ultraviolet light 210 may be mounted in such a way as to minimize light leakage, thereby ensuring that as much UV light as possible is reflected off the skin and into sensor circuit 220. For example, ultraviolet light sensor circuit 220 and ultraviolet light 210 can be mounted at angles to the skin, and focusing prisms (lenses—not shown) may be used to focus the light on the skin and/or the detection sensor.

Figure 3:
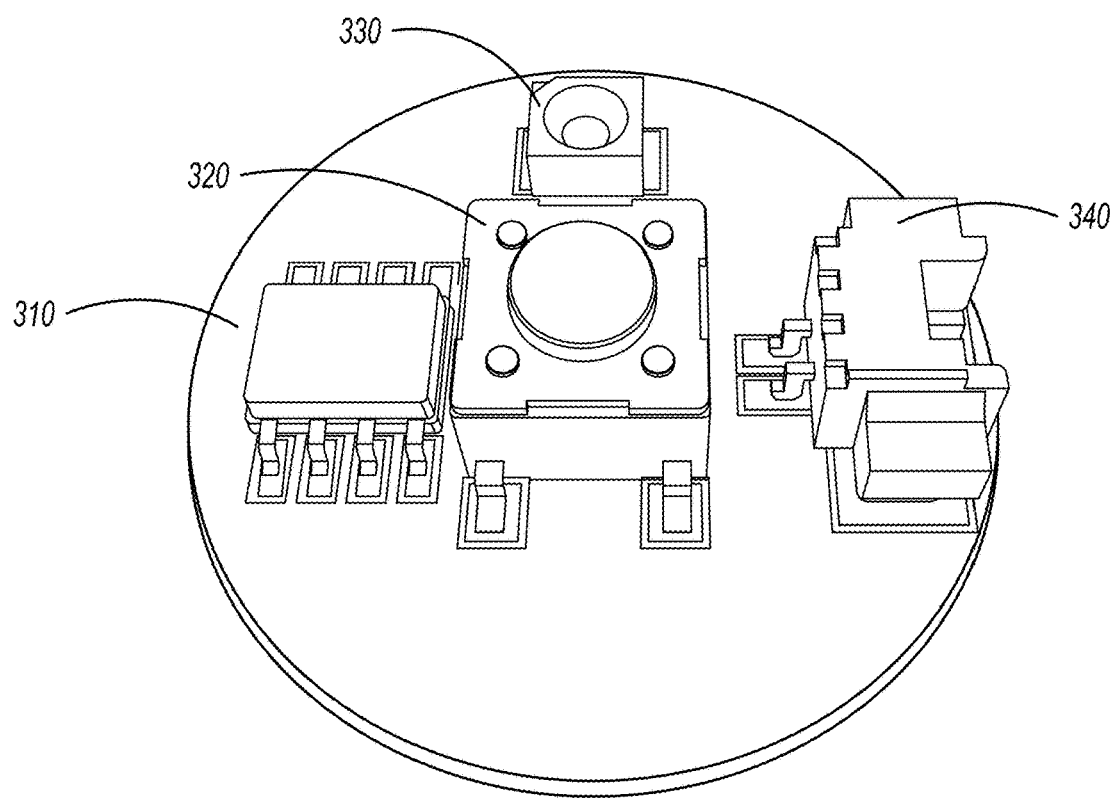
FIG. 3 shows the control/processing circuit of the device, which can be built into the same circuit as that on the skin facing side of the device, according to an aspect of the invention.

FIG. 3 shows the control and processing circuit, which can be built into the same circuit as that shown in FIG. 2. Item 310 is the microprocessor, which can include an integrated Bluetooth (or other means of wired or wireless communication). Item 330 is an LED status light. It may indicate a level of sunscreen protection or other information about device 200, such as if sunscreen coverage is sufficient (green), not sufficient (red), or if the battery needs charging (amber). Item 320 is a momentary on/off switch. When pressed, button 320 may activate the circuit or reset it. Item 340 is a USB-style connector for charging the battery (not shown) and connection to other devices. I/O 340 may be USB or other similar technologies for charging and communicating.

FIG. 4 shows the sunscreen device substrate 410 being integrated into a mobile phone sleeve 400 (sleeve 400 being an exemplary cover). Mobile phone sleeve 400 may be shaped to be removably attached to mobile phone 420. When attached to mobile phone 420, substrate 410 (or portions thereof so as not to disrupt operation of the camera) may be disposed over a camera (not shown) of mobile phone 420. This may be, for example, to use lighting and light shielding abilities of the camera to assist in the techniques described herein. However, placement in front of a camera may not be required as device 200 may not employ anything related to the camera.

Figure 5:
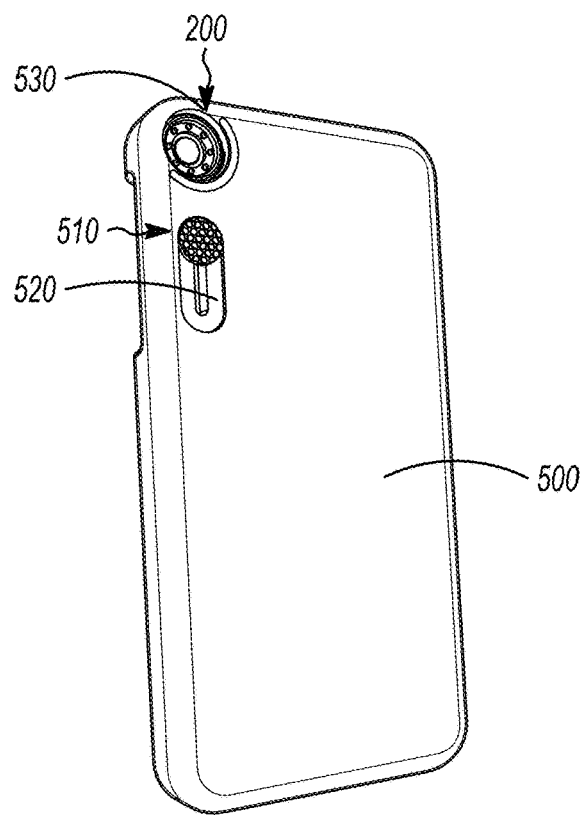
FIG. 5 shows the sunscreen and skin analysis device attached to a smartphone, with the ability to slide the skin and sunscreen analysis portion out of the way, so that the regular smartphone camera can be used, according to an aspect of the invention.

FIG. 5 shows the sunscreen device substrate 410 being integrated, or slideably integrated, into a mobile phone case 500 at location 530 (case 500 being an exemplary cover). Case 500 may further comprise slide 510, disposed within track 520. Slide 510 may be mechanically attached to substrate 410 and slideable within track 520 from a first/active position (as shown in FIG. 5 where substrate 410/device 200 is positioned to be ready for use, such as in front of camera area 530) to a second/inactive position (at the vertical bottom of track 520, and where substrate 410/device 200 is thus positioned for substrated 410/sunscreen device 200 to not be in use, and away from the location 530 or another first/active position). When in the inactive position substrate 410 may be disposed within phone cover 500 or may disposed along or against an interior surface of phone cover (ie near the back of the mobile phone 420, the surface of the mobile phone not having the screen, when it is in case 500).

There is a further device and method to measure sunscreen on skin, as further described below and with respect to FIGS. 6 and 7.

Generally the further device and method distinguishes if sunscreen needs to be re-applied to dark pigmented skin. It uses the previously described technique of measuring the reflection of UV light. Very dark skin naturally absorbs considerable amounts of UV light, so much so that it's been described as having a level of sun burn protection equivalent to SPF 15. Dark skinned people still need to wear sunblock, as protection against cancer causing skin disease, and to prevent burning.

A UV source at one wavelength is aimed at the skin and its reflection is measured (as described herein), the reflection detector may measure the same absorption for very dark skin that is unprotected, as it does for sunscreen protected skin. Example: at 365 nm wavelength, dark skin may absorb 50% of the light, and any skin color with sunscreen Product A will also absorb 50% of the light. Consequently, we don't know if the person is just very dark and her skin naturally absorbs light at this wavelength, or she has sunscreen protection from Product A.

Therefore, we create a "Sunscreen Signature" that is tailored to a specific sunscreen brand, and calculates the relative difference of absorption at more than one wavelength. For example, at 365 nm Product A absorbs 50% of light ("AbsProdA365"=50%), and at 400 nm it absorbs 15% ("AbsProdA400"=15%). We calculate the sunscreen signature ratio of Product A as 0.5/0.15=3.33 (for two known wavelengths). For black skin (without any sunscreen), the absorption at 365 nm and 400 nm is about the same, so the Signature is ~1.00. This highlights that the wavelengths may be selected to know that the skin will absorb roughly the same amount, resulting in a ratio of ~1. By comparing or contrasting the Signature ratio of product ABC with the Signature ratio of untreated skin, we see there is a 3× difference (ie 3.33 divided by 1.00). So our detection method now has sufficient amplitude to detect if sunscreen has been applied. Furthermore, it doesn't provide just a binary response, we can detect sunscreen wearing-off over time. For example, after some amount of sun exposure, when the sunscreen is half-worn off, we would see the sunscreen Signature ratio for Product A drop from 3 to about 1.5 (so the theoretical/initial sunscreen signature ratio of Product A would remain 3 but the measured skin absorption ratio would have dropped from ~3 when Product A was first applied to 1.5) as it reverts to ~1 (ie with effectively no sunscreen coverage). We could also i) take the absorption measurement from the skin at 365 nm divided by AbsProdA365, and if that is much less than one then Product A is wearing off and ii) take the absorption measurement from the skin at 400 nm divided by AbsProdA400, and if that is much less than one then Product A is wearing off. And of course if both are much less than one then there is further basis to conclude Product A is wearing off. When it gets close to 1, we alert the user to reapply sunscreen as "close to 1" may not adequately exceed a threshold (sunscreen reapplication threshold). For example, a signature ratio of about 2 (for example plus or minus 5%) or greater would indicate a level of sunscreen protection of "sufficient" and a signature ratio lower than about 2 (for example plus or minus 5%) would indicate a level of sunscreen protection of "not sufficient". Of course different thresholds and wavelengths may be set for different sunscreen products, manufacturers, users, and the like, and may be relative to baseline absorption properties of particular skin colors (for example a threshold, expressed as absorptions or reflections and percentages or other units of measurement, of a certain amount above a baseline reflection of 10% for black skin with no sunscreen). Finally, because white skin absorbs UV relatively linearly like black skin, this solution works equally well on white skin.

Turning to the figures, FIG. 6 shows four graphs of sunscreen signatures, for sunscreen products A, B, C, and D. A sunscreen signature is an indication of how a sunscreen product absorbs light at different wavelengths. In practice a signature is a set of data points (at least one data point, up to as many as may be desired though in practice only a few may be required to effectively practice aspects of the invention herein) that has an x value of wavelength (nm) and a y value of % absorption.

Product A, for example, has two data points (x,y) of (365, 50) and (400, 15). The data points tell us that Product A absorbs 50% of light at 365 nm when it is properly applied and not degraded and 15% of light at 400 nm when properly applied and not degraded. We may also have a degradation graph (which may allow the device to warn the user, based on the degradation, particular product, and information about the user's skin stored on the device), though that may not be required given our ability to calculate signature ratios (that will tell how much protection is still left given the degradation of the product).

Product B may have two points, just with different values. Product C may have four points within the range of 672. Product D may have four points, all with the same y value. Each of these may be valid signatures to use herein. The signature may be chosen such that the device can have the required number of UV lights, at the required wavelengths, to be able to produce light at the signature wavelengths, and sensors to measure reflected light at those wavelengths. For example, as dark skin typically absorbs light consistently through much of the UV spectrum, a product with high absorption at one wavelength may allow a signature of one wavelength, at such high absorption wavelength. If the measured absorption ratio is anything other than one then the sunscreen must be present. Thus it is a combination of product traits (the signatures) and hardware components and constraints (UV lights and sensors) that may be important in the overall design. Of course different products may require different devices, or devices may be tunable to shine light at several wavelengths based on the signature of the product.

FIG. 7 shows a method of determining sunscreen coverage.

At 702 the sunscreen signature is obtained. This may be, for example, by determining what sunscreen may have been applied. A user may select the sunscreen they believe they applied, by selecting on their phone and/or the device, using an app.

At 704 skin is exposed to one or more lights, at the one or more wavelengths of the signature (for example 365 and 400 for Product A).

At 706 one or more sensors measure absorption at the one or more wavelengths. The results might be something like (365 nm, 39%) and (400, 13).

At 708 the measured absorption is compared to the product absorption. This may be by calculating a measured absorption ratio (calculated as [% AbsAt365]/[% AbsAt400] for the skin, which would be 3 for the above results) for the skin measurement at 706 and comparing it to a product absorption ratio (calculated as [% AbsAt365]/[% AbsAt400] from the Product A signature, which would be 3.33 for the assumed signature).

At this stage, the user's skin could be considered. As noted, a skin absorption ratio (which may be referred to as a skin signature ratio) can be different for different pigments and skin colors. However, generally the skin absorption ratio, for whatever signature is selected (as long as there are at least two lights) is roughly 1. Thus comparing or contrasting the measured skin absorption ratio (3) to the product absorption ratio/sunscreen signature ratio (3.33) would suggest the product is present on the skin. If, when contrasting the sunscreen signature ratio with the skin absorption ratio the difference between the ratios is a material amount then the level of sunscreen protection is insufficient. A material amount may be set by sunscreen manufacturers but may be, for example 1 or greater. And a further check of comparing the measured skin absorption ratio (3) to the skin absorption ratio (1) suggests the product is present. Beyond, in addition to, or instead of contrasting the sunscreen signature ratio with the skin absorption ratio the methods may include ensuring the skin absorption ratio exceeds one or more sunscreen reapplication thresholds. Such may be set based on one or more factors such as a sunscreen manufacturer's preferences, sunscreen signature ratio values and ranges, safety factors, skin colors, and the like, and may be set as absolute differences, percentages differences, and the like.

Of course, it will be readily recognized that provided the measured skin ratio is not 1 then there must be sunscreen present on the skin and if it is close to one then sunscreen needs to be reapplied. This may suffice for present purposes. However, it may also be possible that, if a user indicates they did apply sunscreen the device can be used to determine which product was applied (or which among some set of products). Doing so requires proper sets of UV lights and sensors, but then would allow the measured absorption ratio to be compared to one or more product absorption ratios to find which product was most likely to have been applied.

In practice, a sunscreen manufacturer may:
(a) Select wavelengths based on what sunscreen signature they want and how to most easily measure the presence or lack of sunscreen coverage based on a comparison to skin with no sunscreen. For example they may pick two wavelengths where the skin absorption ratio is 1 while the sunscreen signature ratio is 0.25 or 4 (if the numerator/denominator were reversed). This would make a determination of level of sunscreen protection easier. Of course if the skin absorption ratio for particular wavelengths is not one, then the sunscreen product preferably has a different sunscreen signature ratio at those two wavelengths—again to make a determination of level of sunscreen protection easier.
(b) Select wavelengths that are unique to them and may ensure each of their sunscreen products can be well detected using the device 200 based on those wavelengths (so the sunscreen signature may be somewhat of a brand signature).

It will be apparent to one of skill in the art that other configurations, materials etc may be used in any of the foregoing embodiments of the products, methods, and systems of this invention. It will be understood that the specification is illustrative of the present invention and that other embodiments within the spirit and scope of the invention will suggest themselves to those skilled in the art. All references cited herein are incorporated by reference.

What is claimed is:

1. A sunscreen detection device for detecting the presence of a sunscreen product on a subject's skin, the sunscreen detection device comprising:
   a substrate;
   a cover, wherein the substrate is integrated into the cover, the cover being removably attached to a smartphone;
   a first light, disposed on the substrate and controllably coupled to a processor, controllable by the processor to emit light at a first light wavelength at the subject's skin when the sunscreen detection device is oriented to emit light on the subject's skin;
   a first light sensor circuit, disposed on the substrate and communicatively coupled to the processor, capable of sensing a percentage absorption of light by the subject's skin at the first light wavelength (% AbsAtWL1) and communicating the % AbsAtWL1 to the processor;
   a processor, configured to:
      cause the first light to emit light when the sunscreen detection device is oriented to emit light on the subject's skin;
      record the % AbsAtWL1 from the first light sensor;
      assess a level of sunscreen protection based at least on the % AbsAtWL1; and
      communicate the level of sunscreen protection.

2. The sunscreen detection device of claim 1 wherein the level of sunscreen protection is "sufficient" if % AbsAtWL1 exceeds a first sunscreen reapplication threshold.

3. The sunscreen detection device of claim 1 wherein the processor is further configured to:
   receive a skin color for the subject, the skin color indicating a threshold percentage absorption of light by the subject's skin at the first light wavelength (% ThAtWL1); and
   wherein the assessing is further based on the % ThAtWL1.

4. The sunscreen detection device of claim 3 wherein the level of sunscreen protection is "sufficient" if % AbsAtWL1 exceeds % ThAtWL1 by a second sunscreen reapplication threshold.

5. The sunscreen detection device of claim 3 wherein the receiving is from an input method on the sunscreen device.

6. The sunscreen detection device of claim 3 wherein the receiving is from an app on a user's smartphone, the app being configured to send the skin color to the processor on the sunscreen protection device.

7. The sunscreen detection device of claim 1 further comprising:
   a second light, disposed on the substrate and controllably coupled to a processor, controllable by the processor to emit light at a second light wavelength at the subject's skin when the sunscreen detection device is oriented to emit light on the subject's skin;
   a second light sensor, disposed on the substrate and communicatively coupled to the processor, capable of sensing a percentage absorption of light by the subject's skin at the second light wavelength (% AbsAtWL2) and communicating the % AbsAtWL2 to the processor;
   wherein the processor is further configured to:
      initiate the second light to emit light when the sunscreen detection device is oriented to emit light on the subject's skin;
      obtain the % AbsAtWL2 from the second light sensor;
   and wherein the assessing is further based on the % AbsAtWL2.

8. The sunscreen detection device of claim 7 wherein the assessing further comprises calculating a skin absorption ratio equal to % AbsAtWL1 divided by % AbsAtWL2 and if the skin absorption ratio is about 1 then the level of sunscreen protection is insufficient and if the skin absorption ratio is greater than 2 or less than 0.5 then the level of sunscreen protection is sufficient.

9. The sunscreen detection device of claim 8 further comprising an indicator light capable of producing a set of colors, mounted on the substrate and controllable by the processor and wherein the communicating further comprises the processor lighting the indicator light based on the level of sunscreen protection.

10. The sunscreen detection device of claim 1 wherein the cover further comprises a slide, and wherein the substrate is slideably integrated into the cover and is attached to a slide, and the slide is slideable from an active position, where the sunscreen device is in use, and an inactive position, where the sunscreen device is not in use.

11. A method for detecting the presence of a sunscreen product on a subject's skin, the sunscreen detection device comprising:
   exposing a subject's skin to a first light at a first wavelength and a second light at a second wavelength, the first light and the second light being mounted on, and controllable by, the sunscreen detection device;
   measuring, by a first light sensor and a second light sensor on the sunscreen detection device, an absorption of the first light and an absorption of the second light;
   receiving, by a sunscreen detection device, a sunscreen signature for the sunscreen product, the sunscreen signature comprising the sunscreen product's absorption of light at the first wavelength and the sunscreen product's absorption of light at the second wavelength, wherein the receiving further comprises
      accepting, on an app on a user's smartphone, a user selection of an applied sunscreen product that the user believes they applied;
      locating, by the app on a user's smartphone, the sunscreen signature for the applied sunscreen product; and sending, by the user's smartphone to the sunscreen detection device, the sunscreen signature for the applied sunscreen product to be set as the sunscreen signature for the sunscreen product; and comparing, by a processor on the sunscreen detection device, the absorption of the first light and the absorption of the second light, and using the sunscreen signature, to determine a level of sunscreen protection.

12. The method of claim 11 wherein the comparing comprises calculating a skin absorption ratio equal to the absorption of the first light divided by the absorption of the second light and if the skin absorption ratio is about 1 then the level of sunscreen protection is insufficient.

13. The method of claim 11 wherein the using further comprises:

calculating a sunscreen signature ratio as the sunscreen product's absorption of light at the first wavelength divided by the sunscreen product's absorption of light at the second wavelength; and contrasting the sunscreen signature ratio with the skin absorption ratio and if a difference between the ratios is a material amount then the level of sunscreen protection is insufficient.

14. The method of claim 13 wherein the contrasting further comprises ensuring that the skin absorption ratio is greater than a sunscreen reapplication threshold.

15. The method of claim 11 further comprising:

selecting, by a processor on the sunscreen detection device, the first wavelength and the second wavelength based on the sunscreen signature.

16. The method of claim 14 wherein the selecting further comprises ensuring the sunscreen product's absorption of light at the first wavelength and the sunscreen product's absorption of light at the second wavelength are different.

17. A sunscreen detection device for detecting the presence of a sunscreen product on a subject's skin, the sunscreen detection device comprising:

a substrate wherein the substrate is a round disc, the round disc shaped for installation within a cap of a sunscreen product bottle;

a first light, disposed on the substrate and controllably coupled to a processor, controllable by the processor to emit light at a first light wavelength at the subject's skin when the sunscreen detection device is oriented to emit light on the subject's skin;

a first light sensor circuit, disposed on the substrate and communicatively coupled to the processor, capable of sensing a percentage absorption of light by the subject's skin at the first light wavelength (% AbsAtWL1) and communicating the % AbsAtWL1 to the processor;

a processor, configured to:

cause the first light to emit light when the sunscreen detection device is oriented to emit light on the subject's skin;

record the % AbsAtWL1 from the first light sensor;

assess a level of sunscreen protection based at least on the % AbsAtWL1; and communicate the level of sunscreen protection.

* * * * *